(12) United States Patent
Takahashi

(10) Patent No.: US 10,981,799 B2
(45) Date of Patent: *Apr. 20, 2021

(54) FINE PARTICLES, DISPERSION LIQUID, AND DEODORIZER

(71) Applicant: FUJIFILM Corporation, Tokyo (JP)

(72) Inventor: Kazunori Takahashi, Minami-Ashigara (JP)

(73) Assignee: FUJIFILM Corporation, Tokyo (JP)

( * ) Notice: Subject to any disclaimer, the term of this patent is extended or adjusted under 35 U.S.C. 154(b) by 34 days.

This patent is subject to a terminal disclaimer.

(21) Appl. No.: 16/390,788

(22) Filed: Apr. 22, 2019

(65) Prior Publication Data

US 2019/0248669 A1   Aug. 15, 2019

Related U.S. Application Data

(63) Continuation of application No. PCT/JP2017/037885, filed on Oct. 19, 2017.

(30) Foreign Application Priority Data

Nov. 2, 2016 (JP) .............................. JP2016-215434

(51) Int. Cl.
| | |
|---|---|
| *C01G 3/02* | (2006.01) |
| *C09C 1/00* | (2006.01) |
| *A61L 9/01* | (2006.01) |
| *B82Y 30/00* | (2011.01) |
| *B82Y 40/00* | (2011.01) |

(52) U.S. Cl.
CPC .................. *C01G 3/02* (2013.01); *A61L 9/01* (2013.01); *C09C 1/00* (2013.01); *B82Y 30/00* (2013.01); *B82Y 40/00* (2013.01); *C01P 2002/74* (2013.01); *C01P 2004/64* (2013.01); *C01P 2004/84* (2013.01); *C01P 2006/12* (2013.01); *C01P 2006/22* (2013.01); *C01P 2006/40* (2013.01)

(58) Field of Classification Search
CPC .. C01G 3/02; A61L 9/01; A61L 9/012; B82Y 30/00; B82Y 40/00; C09C 1/0009; C09C 1/00; C01P 2004/04; C01P 2004/03; C01P 2002/85; C01P 2004/50; C01P 2006/12; C01P 2004/64; C01P 2002/74; C01P 2006/22; C01P 2006/40; C01P 2004/84

See application file for complete search history.

(56) References Cited

U.S. PATENT DOCUMENTS

| | | |
|---|---|---|
| 5,707,438 A | 1/1998 | Carlton |
| 2006/0098065 A1 | 5/2006 | Maruyama et al. |
| 2008/0148904 A1* | 6/2008 | Tomonari .................. B22F 9/20 75/247 |
| 2010/0282022 A1 | 11/2010 | Jun et al. |

FOREIGN PATENT DOCUMENTS

| | | | | |
|---|---|---|---|---|
| EP | 3187288 A1 * | 7/2017 | ............ | B22F 1/0014 |
| JP | 63-226357 A | 9/1988 | | |
| JP | 11-507982 A | 7/1999 | | |
| JP | 2009-1474 A | 1/2009 | | |
| JP | 2009-84678 A | 4/2009 | | |
| JP | 2015-190071 A | 11/2015 | | |
| JP | 2016-160124 A | 9/2016 | | |
| WO | WO 2004/050559 A1 | 6/2004 | | |

OTHER PUBLICATIONS

Fujimori et al., Applied and Environmental Microbiology, vol. 2, No. 4, 951-955, (Feb. 2012) (Year: 2012).*
Balamurugan et el., "Surface-modified CuO layer in size-stabilized smole-phase $Cu_2O$ nanopartioles," Applied Physics Letters, vol. 79, No. 19, Nov. 5, 2001, pp. 3176-3178 (4 pages total).
International Preliminary Report on Patentability and Written Opinion of the International Searching Authority (Forms PCT/IB/326, PCT/IB/373 and PCT/ISA/237) for International Application No. PCT/JP2017/037885, dated May 16, 2019, with English translation.
International Search Report (Form PCT/ISA/210) for International Application No. PCT/JP2017/037885, dated Jan. 9, 2018 with English translation.
Japanese Office Action, dated Feb. 12, 2020, for corresponding Japanese Application No. 2018-548622, with an English machine translation.

* cited by examiner

*Primary Examiner* — Robert S Cabral
(74) *Attorney, Agent, or Firm* — Birch, Stewart, Kolasch & Birch, LLP

(57) ABSTRACT

A fine particle in which a surface of a copper oxide fine particle (a) is coated with a coating layer (b) containing a monovalent copper compound, in which the fine particle has a specific surface area of 100 $m^2/g$ or greater, an average primary particle diameter in a range of 5 to 20 nm, and an average secondary particle diameter in a range of 5 to 50 nm, is provided.

20 Claims, 6 Drawing Sheets

FINE PARTICLES 1

FINE PARTICLES 4

FINE PARTICLES, DISPERSION LIQUID, AND DEODORIZER

CROSS REFERENCE TO RELATED APPLICATION

This is a continuation of International Application No. PCT/JP2017/037885 filed on Oct. 19, 2017, and claims priority from Japanese Patent Application No. 2016-215434 filed on Nov. 2, 2016, the entire disclosures of which are incorporated herein by reference.

BACKGROUND OF THE INVENTION

1. Field of the Invention

The present invention relates to fine particles, a dispersion liquid, and a deodorizer.

2. Description of the Related Art

In the related art, metal salt fine particles have been widely used in many fields such as the electronic printing field, the powder metallurgy field, the cosmetic field, the coating material field, the resin processing field, and the like. For example, copper oxide fine particles have been used for nanometal ink for forming substrate wiring of semiconductor circuits obtained by employing a printing technology, which is called printed electronics (PE). Further, with the miniaturization of wiring, it is necessary to stably form fine particles having a particle diameter of several tens of nanometers and copper oxide fine particles with high dispersibility have been required.

As a method of producing nanometer-sized copper oxide fine particles, a method of producing copper oxide using a flow type reaction (flow reactor) has been reported. For example, JP2016-160124A describes a method of producing cupric oxide particles by merging a basic compound into a copper (II) salt solution for reaction.

Further, since the characteristics of metal salt fine particles having a particle diameter of several tens of nanometers or less are greatly different from those of typical metal salt particles, and particularly the surface activity and the surface area are large, the metal salt fine particles have been suggested to be used in the fields of catalysts, adsorbents, and the like.

JP2015-190071A describes that ultrasonic irradiation is performed on a solution obtained by dissolving a metal compound in alcohol with a chelating agent and water, and the metal is chelated and made into fine particles to obtain metal chelate fine particles having excellent antibacterial deodorant performance.

SUMMARY OF THE INVENTION

In a case of metal salt fine particles, particularly nano-sized fine particles having a particle diameter of 100 nm or less, it is difficult to exhibit a deodorizing effect because the particles have high surface activity, are overgrown, and tend to aggregate due to the size effect thereof.

An object of the present invention is to provide nanometer-sized fine particles having an excellent deodorizing effect. Further, another object of the present invention is to provide a dispersion liquid containing the fine particles having an excellent deodorizing effect, which prevents aggregation of the fine particles, and a deodorizer.

As the result of intensive examination conducted by the present inventors in view of the above-described objects, it was found that fine particles having an excellent deodorizing effect are obtained by coating the surface of each copper oxide fine particle (a) with a coating layer (b) containing a monovalent copper compound and respectively setting the specific surface area, the average primary particle diameter, and the average secondary particle diameter to be in a specific range. The present invention has been completed by repeatedly performing examination based on these findings.

In other words, the objects of the present invention are achieved by the following means.

<1> A fine particle in which a surface of a copper oxide fine particle (a) is coated with a coating layer (b) containing a monovalent copper compound, in which the fine particle has a specific surface area of 100 $m^2/g$ or greater, an average primary particle diameter in a range of 5 to 20 nm, and an average secondary particle diameter in a range of 5 to 50 nm.

<2> The fine particle according to <1>, in which a surface of the coating layer (b) containing a monovalent copper compound is further coated with an organic layer (c) derived from an acetic acid or an acetate.

<3> The fine particle according to <1> or <2>, in which the monovalent copper compound is a cuprous oxide.

<4> The fine particle according to any one of <1> to <3>, in which the following peak area ratio (1) of the fine particle in X-ray diffraction using a CuKα as an X-ray source is in a range of 0.01 to 0.10, $$\text{Peak area ratio (1)} = A_1/(A_1+A_2)$$

in which $A_1$ is a peak area of a peak derived from a divalent CuO in a range of 938.5 eV to 948 eV; and $A_2$ is a peak area of a peak derived from all components containing Cu in a range of 928 eV to 938.5 eV <5> The fine particle according to any one of <1> to <4>, in which the fine particle has a zeta potential of 30 mV to 50 mV in a case of being dispersed in water having a pH of 6.8.

<6> A dispersion liquid which is formed by dispersing the fine particle according to any one of <1> to <5> in a dispersion medium, in which a content of the fine particle in the dispersion liquid is in a range of 0.0001% to 14% by mass.

<7> The dispersion liquid according to <6>, in which an average particle diameter of the fine particle in the dispersion liquid according to a dynamic light scattering method is in a range of 5 to 50 nm.

<8> A deodorizer comprising: the fine particle according to any one of <1> to <5>; and the dispersion liquid according to <6> or <7>.

In the present specification, the numerical ranges expressed using "to" indicate ranges including the numerical values described before and after "to" as the lower limits and the upper limits.

In the present specification, the term "copper salt" which is simply described indicates a "copper (II) salt" unless otherwise specified.

In the present specification, the term "fine particles" are not limited to spherical fine particles and may include microstructures with various shapes such as a rod shape and a plate shape.

According to the present invention, it is possible to provide nanometer-sized fine particles having an excellent deodorizing effect. Further, a dispersion liquid containing the fine particles of the present invention and a deodorizer containing these are capable of preventing aggregation of the fine particles and exhibiting the deodorizing effect.

DESCRIPTION OF THE PREFERRED EMBODIMENTS

Figure 1:
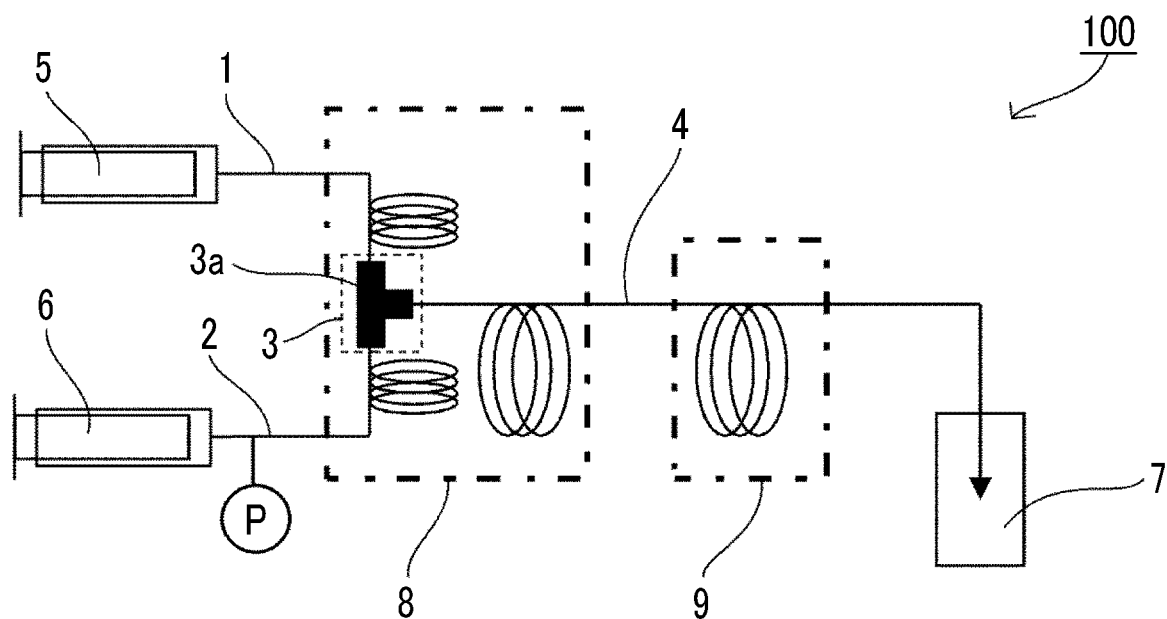
FIG. 1 is a flow diagram illustrating a preferred embodiment of a method of producing fine particles according to the present invention.

Hereinafter, fine particles, a dispersion liquid, and a deodorizer of the present invention will be described in detail. Further, "fine particles of the present invention in which the surface of each copper oxide fine particle (a) is coated with a coating layer (b) containing a monovalent copper compound" are simply referred to as "copper oxide fine particles" in some cases.

<Fine Particles>

The fine particles of the present invention are fine particles in which the surface of each copper oxide fine particle (a) is coated with the coating layer (b) containing a monovalent copper compound, in which the specific surface area thereof is 100 m²/g or greater, the average primary particle diameter thereof is in a range of 5 to 20 nm, and the average secondary particle diameter thereof is in a range of 5 to 50 nm.

As the copper oxide fine particles (a), copper oxide fine particles formed of an oxide of monovalent or divalent copper containing copper (I) oxide particles ($Cu_2O$ particles) as a main component are preferable, and copper (I) oxide particles ($Cu_2O$ particles), copper (II) oxide particles (CuO particles), or a mixture of copper (I) oxide particles and copper (II) oxide particles is more preferable. Here, the main component indicates that the amount thereof is in a range of 50% to 100% by weight, preferably in a range of 70% to 100% by weight, and more preferably in a range of 85% to 100% by weight of the copper oxide fine particles (a).

The surface of each copper oxide fine particle (a) is coated with the coating layer (b). A part or all of the surface of each copper oxide fine particle (a) may be coated with the coating layer (b).

The surface of the copper oxide fine particle (a) being coated with the coating layer (b) containing a monovalent copper compound can be confirmed from the presence of a peak derived from divalent CuO in a range of 938.5 eV to 948 eV in the $Cu_2p_{3/2}$ spectrum according to X-ray photoelectron spectroscopy (XPS).

The coating layer (b) contains a monovalent copper compound and it is preferable that the coating layer (b) contains a monovalent copper compound as a main component. As the monovalent copper compound, cuprous oxide is preferable. Here, the main component indicates that the amount thereof is in a range of 30% to 100% by weight, preferably in a range of 50% to 100% by weight, more preferably in a range of 70% to 100% by weight, and most preferably in a range of 85% to 100% by weight of the coating layer (b). The coating layer (b) may contain copper hydroxide, salts derived from raw materials, and the like as components other than the monovalent copper compound.

The average primary particle diameter is a value obtained by measuring the diameter of each primary particle from an image of an electron microscope and averaging the diameters of 90% of primary particles obtained by removing 5% of primary particles on a side where the diameters thereof are the smallest and 5% of primary particles on a side where the diameters thereof are the largest from among the total number of primary particles. Here, the diameter indicates a circumscribed circle equivalent diameter of each primary particle.

The average primary particle diameter of the fine particles according to the embodiment of the present invention is in a range of 5 to 20 nm, preferably in a range of 5 to 15 nm, and more preferably in a range of 5 to 10 nm. In a case where the average primary particle diameter thereof is in a range of 5 to 20 nm, fine particles having an excellent deodorizing effect are obtained.

Secondary particles are defined as an aggregate formed by the primary particles being fused or brought into contact with one another. The average secondary particle diameter is a value obtained by measuring the diameter of each secondary particle from an image of an electron microscope and averaging the diameters of 90% of secondary particles obtained by removing 5% of fine particles on a side where the diameters thereof are the smallest and 5% of fine particles on a side where the diameters thereof are the largest from among the total number of secondary particles.

Here, the diameter indicates a circumscribed circle equivalent diameter of each secondary particle.

The average secondary particle diameter of the fine particles according to the embodiment of the present invention is in a range of 5 to 50 nm, preferably in a range of 15 to 50 nm, and more preferably in a range of 20 to 50 nm. In a case where the average secondary particle diameter thereof is in a range of 5 to 50 nm, fine particles having an excellent deodorizing effect are obtained.

The average particle diameter of the fine particles can be measured by dynamic light scattering with a particle size distribution measuring machine that performs measurement using laser diffraction.

It is preferable that the copper oxide fine particle (a) is protected by an organic layer (c) derived from acetic acid or an acetate and more preferable that the surface of the coating layer (b) containing a monovalent copper compound is coated with the organic layer (c) derived from acetic acid or an acetate. In this manner, in a case where the fine particles according to the embodiment of the present invention are dispersed in a dispersion medium, since the particles repel one another due to the charge protected by the organic layer (c) derived from acetic acid or an acetate, aggregation is suppressed, copper oxide fine particles are stabilized without precipitation even in a case where a dispersant is not added or a dispersion treatment is not performed so that a dispersion liquid with excellent dispersibility is obtained.

The organic layer (c) is a layer containing an organic substance, as a main component, derived from acetic acid or an acetate. Here, the main component indicates that the amount thereof is in a range of 30% to 100% by weight, preferably in a range of 50% to 100% by weight, more preferably in a range of 70% to 100% by weight, and most preferably in a range of 85% to 100% by weight of the organic layer (c). Examples of the organic substance derived from acetic acid or an acetate include sodium acetate and lithium acetate. Further, the organic layer (c) may contain copper salts derived from raw materials as components other than the organic substance derived from acetic acid or an acetate.

The presence of the organic layer (c) can be confirmed by time-of-flight secondary ion mass spectrometry (TOF-SIMS).

In the fine particles according to the embodiment of the present invention, it is preferable that a peak area ratio (1) in X-ray diffraction using CuKα as an X-ray source is in a range of 0.01 to 0.10.

Peak area ratio $(1)=A_1/(A_1+A_2)$ $A_1$: a peak area of a peak derived from divalent CuO in a range of 938.5 eV to 948 eV $A_2$: a peak area of a peak derived from all components containing Cu in a range of 928 eV to 938.5 eV In a case where the peak area ratio (1) is set to be in the above-described range, there is an advantage that each fine particle according to the embodiment of the present invention is easily coated with the organic layer (c) derived from acetic acid or an acetate and the fine particles can be stably dispersed in a dispersion medium.

The specific surface area of the fine particles according to the embodiment of the present invention is 100 m$^2$/g or greater and more preferably in a range of 100 to 250 m$^2$/g. In a case where the specific surface area thereof is in the above-described range, fine particles with an excellent deodorizing effect are obtained. The specific surface area can be measured according to the BET one-point method.

The shape of the fine particles according to the embodiment of the present invention is not particularly limited as long as the fine particles are particulate. The term "particulate" indicates a small particle shape, and specific examples thereof include a spherical shape, an ellipsoidal shape, a rod shape, and a plate shape. The fine particles do not necessarily have a perfect spherical or ellipsoidal shape, and a part thereof may be distorted. It is advantageous that the fine particles have a spherical shape rather than a rod shape or a plate shape from the viewpoint that the contact area between particles is decreased so that aggregation is unlikely to occur.

The fine particles according to the embodiment of the present invention have a zeta potential of 30 mV to 50 mV in a case of being dispersed in water having a pH of 6.8. In a case where the zeta potential is in the above-described range, the dispersibility becomes excellent so that aggregation of the particles in the dispersion liquid is unlikely to occur. Therefore, fine particles having a desired particle diameter can be obtained. The zeta potential can be measured according to a known method.

The applications of the fine particles according to the embodiment of the present invention and the dispersion liquid containing the fine particles are not particularly limited, and the fine particles and the dispersion liquid can be used for various applications such as metal ink for forming substrate wiring, copper supply sources for electroless plating, ceramic raw materials such as superconductors, pigments, colorants, and glazes.

<Dispersion Liquid>

The present invention also relates to a dispersion liquid.

The dispersion liquid according to the embodiment of the present invention is a dispersion liquid obtained by dispersing the fine particles according to the embodiment of the present invention in a dispersion medium, and the content of the fine particles in the dispersion liquid is in a range of 0.0001% to 14% by mass, preferably in a range of 0.0001% to 10% by mass, more preferably in a range of 0.0005% to 5% by mass, and particularly preferably in a range of 0.0005% to 1% by mass.

In the dispersion liquid according to the embodiment of the present invention, some of the fine particles according to the embodiment of the present invention may become dispersed particles by being aggregated and dispersed. The average particle diameter of the fine particles in the dispersion liquid can be measured by dynamic light scattering with a particle size distribution measuring machine that performs measurement using laser diffraction. The average particle diameter of the fine particles in the dispersion liquid is 70 nm or less, preferably in a range of 1 to 60 nm, and more preferably in a range of 5 to 50 nm. In a case where the average particle diameter of the copper oxide fine particles are in the above-described range, the dispersibility becomes excellent so that the precipitation of aggregates can be suppressed.

[Dispersion Medium]

As the dispersion medium of the dispersion liquid according to the embodiment of the present invention, water, an organic solvent, or a mixture of water and an organic solvent can be used, and those exemplified as the solvent in the method of producing the copper oxide fine particles can also be exemplified. Among these, water or an alcohol solution is preferable, and water is more preferable.

[Additive]

The dispersion liquid according to the embodiment of the present invention may contain additives as necessary. Examples of the additives include known additives such as an ultraviolet absorbing agent, a preservative, a pH adjuster, an antifoaming agent, a dispersant, and a dispersion stabilizer.

As the dispersant which can be used as the dispersion liquid according to the embodiment of the present invention, for example, an anionic, cationic, amphoteric, or non-ionic dispersant, or a low-molecular-weight or high-molecular-weight dispersant can be used. Preferred examples thereof include sodium hexametaphosphate. The amount of the dispersant to be added may be appropriately adjusted depending on the type of the dispersant, but the amount of the dispersant to be added to the dispersion liquid is preferably in a range of 0% to 10% by mass (wt %) and more preferably in a range of 0% to 8% by mass.

<Production of Fine Particles>

A method of producing the fine particles according to the embodiment of the present invention is not particularly limited, but it is preferable that the fine particles are continuously produced by a flow type reaction. The method of producing the fine particles according to the embodiment of the present invention will be described below with reference to the accompanying drawings.

FIG. 1 illustrates a preferred flow type reaction system (100) for producing the fine particles according to the embodiment of the present invention. The flow type reaction system (100) illustrated in FIG. 1 includes a first flow path (1) through which a copper salt solution circulates; a second flow path (2) through which a basic compound solution circulates; a merging region (3) where the first flow path (1) is merged with the second flow path (2); and a reaction flow path (4) connected to the downstream of the merging region (3).

In the embodiment illustrated in FIG. 1, copper salt solution introduction means (5) for introducing the copper salt solution into the first flow path (1) is disposed upstream of the first flow path (1), and basic compound solution introduction means (6) for introducing the basic compound solution into the second flow path (2) is disposed upstream of the second flow path (2). The copper salt solution introduction means (5) and the basic compound solution introduction means (6) are not particularly limited, and various pumps can be used. Among these, from the viewpoint of controlling the flow rate with high accuracy, a syringe pump can be suitably used. The same applies to third liquid introduction means (11) described below.

Figure 2:
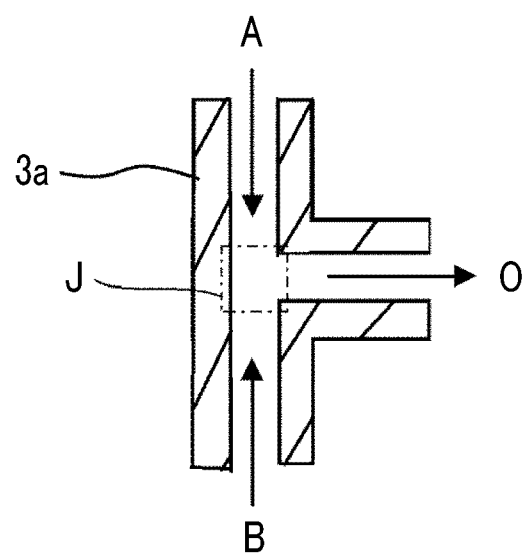
FIG. 2 is a cross-sectional view illustrating a T-shaped mixer which is installed in a merging area in the embodiment of FIG. 1.

In the embodiment illustrated in FIG. 1, a T-shaped mixer (3a) is disposed in the merging region (3). FIG. 2 is a cross-sectional view illustrating a state of solution merging using the T-shaped mixer (3a). As illustrated in FIG. 2, the copper salt solution circulating through the first flow path (1) and the basic compound solution circulating through the second flow path (2) are respectively introduced into the T-shaped mixer (3a) from an A side (opening portion A) and a B side (opening portion B) of the T-shaped mixer (3a). The copper salt solution and the basic compound solution introduced into the T-shaped mixer (3a) are merged with each other in a merging portion J in the T-shaped mixer (3a), and this merged solution flows out toward an (O) side of the T-shaped mixer and is introduced into the reaction flow path (4).

In a case where the copper salt solution is merged with the basic compound solution in the T-shaped mixer (3a), the copper salt reacts with the basic compound so that copper hydroxide ($Cu(OH)_2$) is generated. Next, this copper hydroxide is dehydrated by being heated and then copper oxide fine particles are generated. These reactions proceed while the merged solution circulates through the reaction flow path (4) from when the copper salt and the basic compound are brought into contact with each other. The details of the reactions and the reaction conditions will be described below.

The copper oxide fine particles generated in the reaction flow path are recovered in a recovery container 7 as a copper oxide fine particle dispersion liquid.

Figure 3:
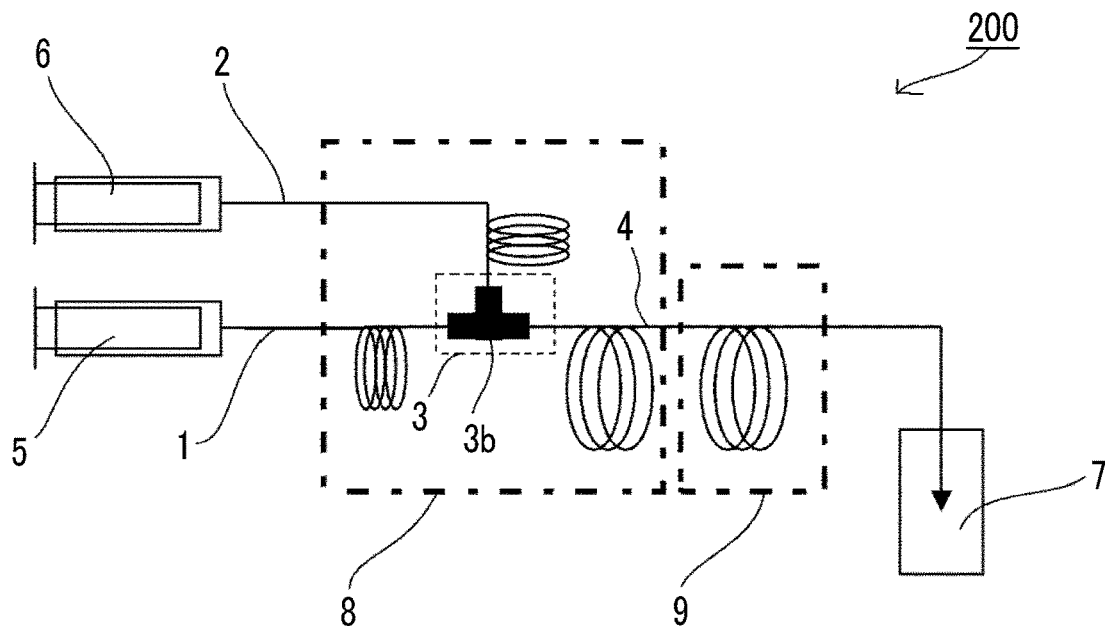
FIG. 3 is a flow diagram illustrating another preferred embodiment of the method of producing fine particles according to the present invention.

FIG. 3 illustrates another preferred flow type reaction system (200) for producing the fine particles according to the embodiment of the present invention. The flow type reaction system (200) illustrated in FIG. 3 includes a first flow path (1) through which a copper salt solution circulates; a second flow path (2) through which a basic compound solution circulates; a merging region (3) where the first flow path (1) is merged with the second flow path (2); and a reaction flow path (4) connected to the downstream of the merging region (3).

In the embodiment illustrated in FIG. 3, copper salt solution introduction means (5) for introducing the copper salt solution into the first flow path (1) is disposed upstream of the first flow path (1), and basic compound solution introduction means (6) for introducing the basic compound solution into the second flow path is disposed upstream of the second flow path (2).

Figure 4:
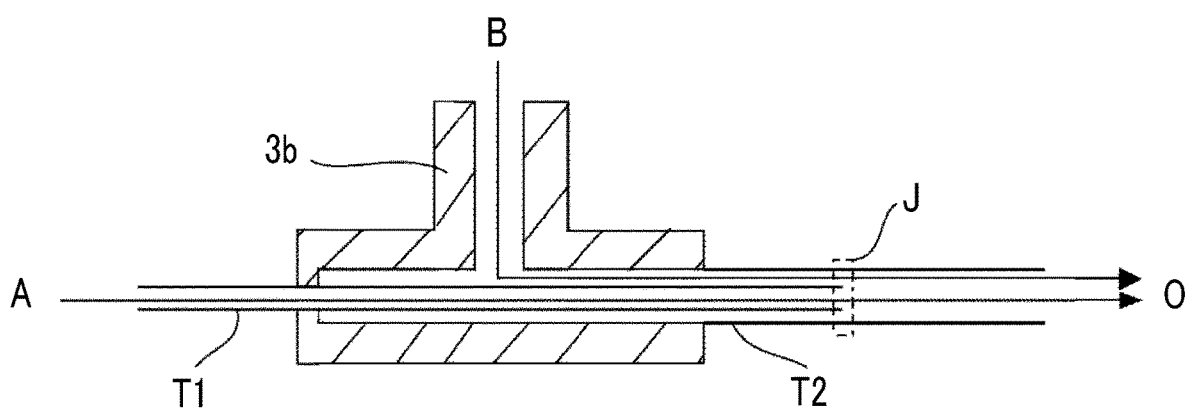
FIG. 4 is a cross-sectional view illustrating a two-layer cylindrical mixer which is installed in a merging area in the embodiment of FIG. 3.

In the embodiment illustrated in FIG. 3, a two-layer cylindrical mixer (3b) is disposed in the merging region (3). FIG. 4 is a cross-sectional view illustrating a state of solution merging using the two-layer cylindrical mixer (3b). The first flow path (1) is connected to an A side (opening portion A) of an inner tube (T1) passing through the two-layer cylindrical mixer (3b) or the first flow path (1) itself is integrated with the inner tube (T1). In this manner, the copper salt solution circulating through the first flow path (1) circulates from the A side to an O side in the inner tube (T1).

Meanwhile, the second flow path (2) is connected to an introduction portion B (opening portion B) of the two-layer cylindrical mixer (3b). In this manner, the basic compound solution having circulated through the second flow path (2) fills the space between the outer tube (T2) and the inner tube (T1) of the two-layer cylindrical mixer (3b) and circulates toward the O side.

The copper salt solution circulating through the inner tube (T1) toward the O side is merged with the basic compound solution having circulated through the space between the outer tube (T2) and the inner tube (T1) toward the O side in an end portion (merging portion J) of the O side in the inner tube (T1) and is introduced into the reaction flow path (4) connected to the downstream thereof.

Figure 5:
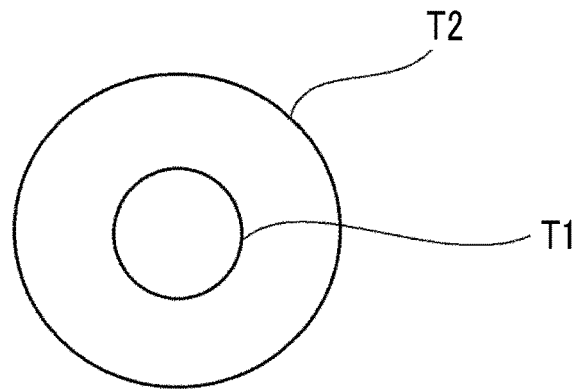
FIG. 5 is a view illustrating a merging portion J of the two-layer cylindrical mixer illustrated in FIG. 4 at the time of being viewed from a side of O.

FIG. 5 illustrates a cross section at the time of viewing the merging portion J in FIG. 4 from the O side. In FIG. 5, the copper salt solution circulates through in the inner tube T1, and the basic compound solution circulates through the space between the outer tube T2 and the inner tube T1.

In a case where the copper salt solution is merged with the basic compound solution in the two-layer cylindrical mixer (3b), the copper salt reacts with the basic compound so that copper hydroxide ($Cu(OH)_2$) is generated. Next, this copper hydroxide is dehydrated by being heated and then copper oxide fine particles are generated. These reactions proceed while the merged solution circulates through the reaction flow path (4) from when the copper salt and the basic compound are brought into contact with each other. The details of the reactions and the reaction conditions will be described below.

In the form illustrated in FIG. 4, the copper salt solution and the basic compound solution being merged with each other in the merging portion J may be introduced into the reaction flow path (4) in a laminar flow state and then circulate through the reaction flow path or may be merged with each other in a state of gradually being mixed while circulating through the reaction flow path (4). Further, the copper salt solution and the basic compound solution may be quickly mixed by causing turbulent flow at the merging portion J and then flow into the reaction flow path (4). As illustrated in FIG. 4, in a case where two liquids are merged with each other using the two-layer cylindrical mixer, since the contact between the copper salt and the basic compound does not occur on the outer wall of the tube in the mixer, copper oxide is not deposited on the outer wall of the tube in the mixer. Therefore, the pressure is unlikely to be increased during the flow reaction, and cupric oxide can be continuously and more stably produced.

In the embodiments illustrated in FIGS. 3 to 5, the copper salt solution may be allowed to circulate through the space between the outer tube (T2) and the inner tube (T1) and the basic compound solution may be allowed to circulate through the inner tube T1. This form is also preferable as the method of producing the fine particles according to the embodiment of the present invention.

Figure 6:
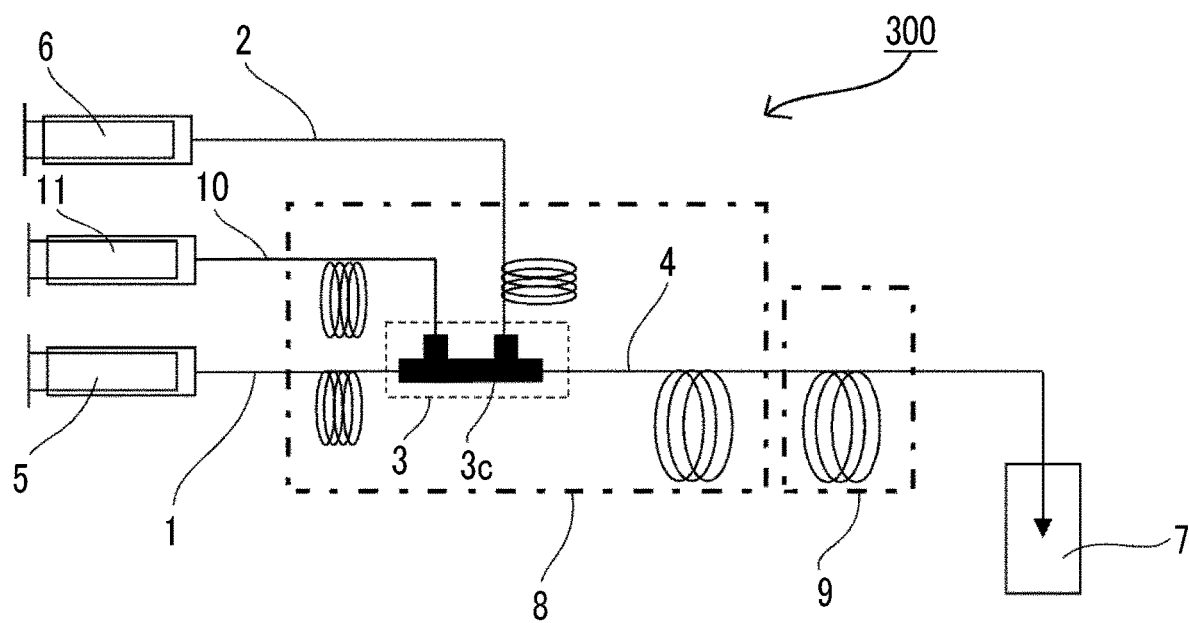
FIG. 6 is a flow diagram illustrating still another preferred embodiment of the method of producing fine particles according to the present invention.

FIG. 6 illustrates still another preferred flow type reaction system (300) for the method of producing the fine particles according to the embodiment of the present invention. The flow type reaction system (300) illustrated in FIG. 6 includes a first flow path (1) through which a copper salt solution circulates; a second flow path (2) through which a basic compound solution circulates; a third flow path (10) through which a third liquid described below circulates; a merging region (3) where the first flow path (1), the second flow path (2), and the third flow path (10) are merged; and a reaction flow path (4) connected to the downstream of the merging region (3).

In the embodiment illustrated in FIG. 6, copper salt solution introduction means (5) for introducing the copper salt solution into the first flow path (1) is disposed upstream of the first flow path (1), basic compound solution introduction means (6) for introducing the basic compound solution into the second flow path is disposed upstream of the second flow path (2), and third liquid introduction means (11) for introducing the third liquid into the third flow path (10) is disposed upstream of the third flow path (10).

Figure 7:
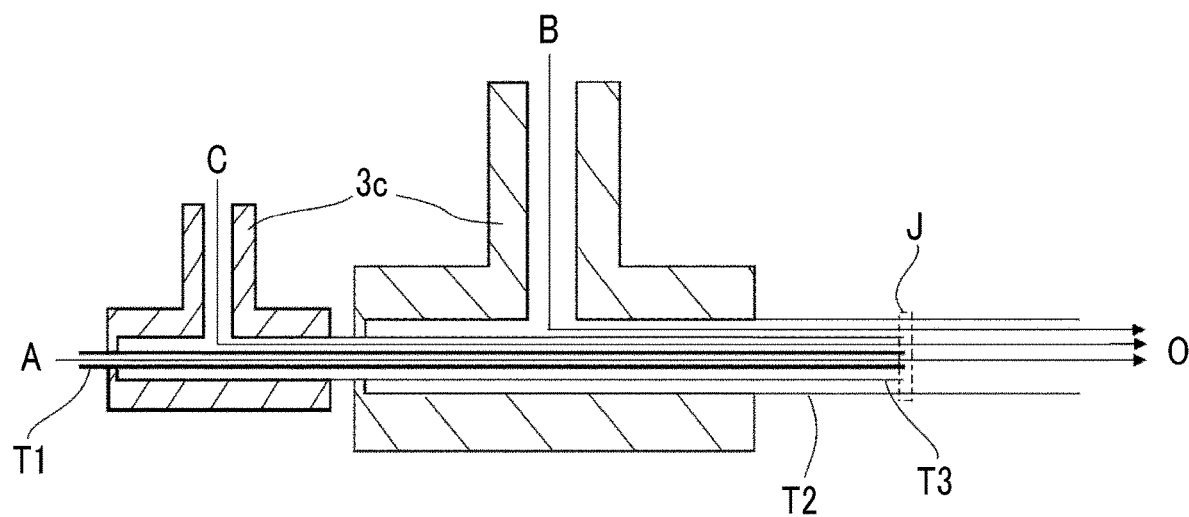
FIG. 7 is a cross-sectional view illustrating a three-layer cylindrical mixer which is installed in a merging area in the embodiment of FIG. 6.

In the embodiment illustrated in FIG. 6, a three-layer cylindrical mixer (3c) is disposed in the merging region (3). FIG. 7 is a cross-sectional view illustrating solution merging using the three-layer cylindrical mixer (3c). The first flow path (1) is connected to an A side (opening portion A) of an inner tube (T1) passing through the three-layer cylindrical mixer (3c) or the first flow path (1) itself is integrated with the inner tube (T1). In this manner, the copper salt solution circulating through the first flow path (1) circulates from the A side to an O side in the inner tube (T1).

Further, the third flow path (10) is connected to an introduction portion C (opening portion C) of the three-layer cylindrical mixer (3c). In this manner, the third liquid having circulated through the third flow path (10) fills the space between a middle tube (T3) and the inner tube (T1) of the three-layer cylindrical mixer (3c) and circulates toward the O side.

Further, the second flow path (2) is connected to an introduction portion B (opening portion B) of the three-layer cylindrical mixer (3c). In this manner, the basic compound solution having circulated through the second flow path (2) fills the space between the middle tube (T3) and the outer tube (T2) of the three-layer cylindrical mixer (3c) and circulates toward the O side.

The copper salt solution circulating through the inner tube (T1) toward the O side is merged with the third liquid having circulated through the space between the middle tube (T3) and the inner tube (T1) toward the O side and the basic compound solution having circulated through the space between the outer tube (T2) and the middle tube (T3) toward the O side in an end portion (merging portion J) of the O side in the inner tube (T1) and is introduced into the reaction flow path (4) connected to the downstream thereof.

Figure 8:
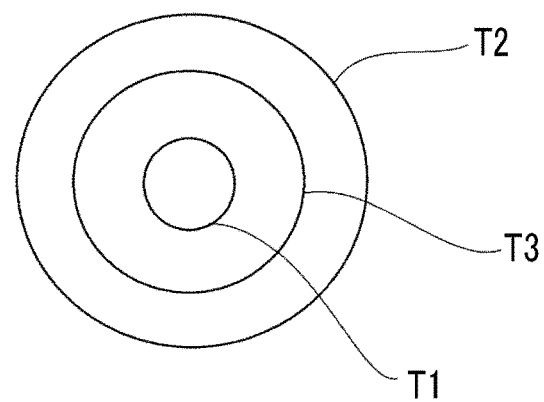
FIG. 8 is a view illustrating a merging portion J of the three-layer cylindrical mixer illustrated in FIG. 7 at the time of being viewed from a side of O.

FIG. 8 illustrates a cross section at the time of viewing the merging portion J in FIG. 7 from the O side. In FIG. 8, the copper salt solution circulates through in the inner tube (T1), the third liquid circulates through the space between the middle tube (T3) and the inner tube (T1), and the basic compound solution circulates through the space between the outer tube (T2) and the middle tube (T3).

In the form illustrated in FIG. 6, the third liquid is present between the copper salt solution and the basic compound solution in the merging portion J. Examples of the third liquid include water, an organic solvent, an acidic compound solution, a copper salt solution, a basic compound solution, a solution containing a dispersion stabilizer, and a mixed solution of these.

In a case where water is used as the third liquid, the contact between the copper and the base at a high concentration can be prevented so that concentration unevenness of the reaction solution can be alleviated.

In a case where an acidic solution (for example, a solution containing a carboxylic acid compound such as hydrochloric acid, sulfuric acid, nitric acid, or acetic acid) is used as the third liquid, the pH of the reaction solution can be controlled.

In a case where a solution containing a dispersion stabilizer is used as the third liquid, the particle growth of cupric oxide to be generated is controlled so that the shape thereof is adjusted, and the particle size or the dispersion stability can be controlled. The dispersion stabilizer is not particularly limited, and known compounds which can function as a dispersion stabilizer can be used. Examples thereof include a diol such as ethylene glycol, carboxylic acid such as olefic acid or oleate, an amine such as oleylamine or an oleylamine salt, a compound containing thiol, a polymer compound such as gelatin, and typical organic solvents.

In the form illustrated in FIG. 7, the copper salt solution and the basic compound solution being merged with each other in the merging portion J may be introduced into the reaction flow path (4) in a laminar flow state and then circulate through the reaction flow path or may be gradually mixed while circulating through the reaction flow path (4). Further, the copper salt solution and the basic compound solution may be quickly mixed by causing turbulent flow in the merging portion J and then flow into the reaction flow path (4).

As illustrated in FIG. 7, in a case where the copper salt solution and the basic compound solution are merged with each other using the three-layer cylindrical mixer, since the contact between the copper salt and the basic compound does not occur on the outer wall of the tube in the mixer, copper oxide is not deposited on the outer wall of the tube in the mixer. Therefore, an increase in the pressure during the flow reaction can be suppressed, and cupric oxide can be continuously and more stably produced.

In the embodiments illustrated in FIGS. 6 to 8, the copper salt solution may be allowed to circulate through the space between the outer tube (T2) and the middle tube (T3) and the basic compound solution may be allowed to circulate through the inner tube (T1). This form is also preferable as an embodiment of the method of producing the fine particles according to the embodiment of the present invention. Further, a form in which the copper salt solution is allowed to circulate through the space between the outer tube (T2) and the middle tube (T3), the basic compound solution is allowed to circulate through the space between the middle tube (T3) and the inner tube (T1), and the copper salt solution is allowed to circulate through the inner tube or a form in which the basic compound solution is allowed to circulate through the space between the outer tube (T2) and the middle tube (T3), the copper salt solution is allowed to circulate through the space between the middle tube (T3) and the inner tube (T1), and the basic compound solution is allowed to circulate through the inner tube is employed, the contact interface between the copper salt solution and the basic compound solution is increased and diffusion mixing efficiency after merging can be further increased.

Next, the configurations of each member in the above-described embodiments and the reactions for generating the copper oxide fine particles will be sequentially described.

[Upstream Side Flow Path in Merging Region]

The shape of each flow path (the first flow path (1), the second flow path (2), and the third flow path (10) in the embodiments illustrated in FIGS. 1, 3, and 6) disposed on the upstream side of the merging region (3) is not particularly limited. Typically, a tube having an equivalent diameter of 0.1 cm to 50 cm (preferably in a range of 0.1 cm to 10 cm) and a length of 20 cm to 50 m is used. The cross-sectional shape of the flow path is not particularly limited, and examples thereof include a circular shape, an elliptical shape, and polygonal shapes such as a rectangular shape and a square shape. From the viewpoint that the liquid pool is unlikely to occur in the tube, it is more preferable that the cross-sectional shape of the flow path is circular.

In the present specification, the equivalent diameter is a diameter in a case where the flow path cross section is converted into a circle. The "equivalent diameter" is also referred to as the equivalent particle size and is a term used in the field of mechanical engineering. At the time of assuming a circular tube equivalent to a tube or flow path having an optional cross-sectional shape in the tube, the diameter of the cross section in the equivalent circular tube is referred to as the equivalent diameter. The equivalent diameter ($d_{eq}$) is defined as $d_{eq}=4A/p$ in a case where the cross-sectional area in the tube is set as A and the wetted perimeter length (inner circumference length) of the tube is set as p. In a case where this equivalent diameter is applied to a circular tube, the equivalent diameter matches the diameter of the cross section in the circular tube. Based on data of the equivalent circular tube, the equivalent diameter is used to estimate the flow or heat transfer characteristics of the tube and indicates a spatial scale (representative length) of the phenomenon. The equivalent diameter becomes $d_{eq}=4a^2/4a=a$ in a case where the cross section in the tube has a regular square tube shape with one side of a, $d_{eq}=a/3^{1/2}$ in a case where the cross section in the tube has an equilateral triangle shape with one side of a, and $d_{eq}=2h$ in a case of flow between parallel flat plates with a flow path height of h (for example, see "Mechanical Engineering Dictionary" edited by The Japan Society of Mechanical Engineering, 1997, Maruzen Inc.).

The material of the tube constituting the flow path is not particularly limited, and examples thereof include perfluoroalkoxyalkane (PFA), TEFLON (registered trademark), an aromatic polyether ketone-based resin, stainless steel, copper (or an alloy thereof), nickel (or an alloy thereof), titanium (or an alloy thereof), quartz glass, and lime soda glass. From the viewpoints of the flexibility and the chemical resistance, PFA, TEFLON (registered trademark), stainless steel, nickel alloy (hastelloy), or titanium is preferable as the material of the tube.

[T-Shaped Mixer]

The T-shaped mixer (3a) is a structure of a T-shaped tube. As described above, the T-shaped mixer is used in the embodiment illustrated in FIG. 1. In the T-shaped mixer, among three opening portions (A, B, and O in FIG. 2) included in the T-shaped mixer, the first flow path is connected to only one optional opening portion. Further, the connecting portion to which the second flow path is connected may be any one of two opening portions excluding the opening portion to which the first flow path is connected.

It is preferable that the first flow path and the second flow path may be respectively connected to opening portions (in other words, the opening portion A and the opening portion B in FIG. 2) facing each other in the T-shaped mixer.

The material of the T-shaped mixer is not particularly limited, and examples thereof include perfluoroalkoxyalkane (PFA), TEFLON (registered trademark), an aromatic polyether ketone-based resin, stainless steel, copper (or an alloy thereof), nickel (or an alloy thereof), titanium (or an alloy thereof), quartz glass, and lime soda glass.

The cross-sectional shape of the opening portion of the T-shaped mixer is not particularly limited, and examples thereof include a circular shape, an elliptical shape, and polygonal shapes such as a rectangular shape and a square shape. From the viewpoint that the liquid pool is unlikely to occur in the mixer, it is more preferable that the cross-sectional shape of the tube in the T-shaped mixer is circular.

From the viewpoints of the mixing performance and the pressure drop, the equivalent diameter of the opening portion of the T-shaped mixer is preferably in a range of 0.1 mm to 5 mm and more preferably in a range of 0.2 mm to 2 mm. The equivalent diameters of three opening portions of the T-shaped mixer may be the same as or different from one another.

Examples of commercially available products of the T-shaped mixer which can be used include UNION TEE (manufactured by Swagelok Company), low depth volume type UNION TEE (manufactured by Swagelok Company), TEE UNION (manufactured by Upchurch Scientific Inc.), Three-way Joint (manufactured by Tokyo Rikakikai Co., Ltd.), Micro-Volume Connector (manufactured by VICI Valco), and Nano-Volume Fitting (manufactured by VICI Valco).

[Multilayer Cylindrical Mixer]

A multilayer cylindrical mixer can be used in the merging region (3) where the copper salt solution is merged with the basic compound solution. FIGS. 3 to 8 illustrate embodiments in which the two-layer cylindrical mixer (3b) and the three-layer cylindrical mixer (3c) are used as the multilayer cylindrical mixer as described above.

A multilayer cylindrical mixer provided with four or more layers may be used in the merging region (3). As illustrated in FIGS. 4 and 7, the multilayer cylindrical mixer is a structure which includes tubes having a multilayer structure formed such that flow paths are provided between tubes; and an inlet for introducing a liquid into a flow path (a flow path between an inner tube and an outer tube) outside a minimum tube (inner tube). In the multilayer cylindrical mixer, the flow path through which the copper salt solution circulates and the flow path through which the basic compound solution circulates may be adjacent to each other, or a third liquid (for example, a pH adjuster such as water, an organic solvent, or an acid, a dispersant solution, a second copper salt solution, or a second basic compound solution) which plays a role of adjusting the mixing, the reactions, and the dispersed state of generated particles is allowed to circulate through the flow path between the flow path through which the copper salt solution circulates and the flow path through which the basic compound solution circulates.

In a case where the multilayer cylindrical mixer is used, each solution introduced into the mixer can be merged as laminar flow toward the downstream of the mixer as illustrated n FIGS. 4 and 7. Each solution merged as laminar flow may flow in the reaction flow path in a laminar flow state or may flow in the reaction flow path by being mixed using turbulent flow gradually or immediately after being merging.

The material of the multilayer cylindrical mixer is not particularly limited, and examples thereof include perfluoroalkoxyalkane (PFA), TEFLON (registered trademark), an aromatic polyether ketone-based resin, stainless steel, copper (or an alloy thereof), nickel (or an alloy thereof), titanium (or an alloy thereof), quartz glass, and lime soda glass.

The cross-sectional shape of the tube or the opening portion of the multilayer cylindrical mixer is not particularly limited, and examples thereof include a circular shape, an elliptical shape, and polygonal shapes such as a rectangular shape and a square shape. From the viewpoint that the liquid pool is unlikely to occur in the mixer, it is more preferable that the cross-sectional shape of the tube in the multilayer cylindrical mixer is circular.

The equivalent diameter of a minimum cylinder (inner tube) of the multilayer cylindrical mixer is preferably in a range of 0.1 mm to 50 mm and more preferably in a range of 0.2 mm to 10 mm. Further, the equivalent diameter of an outermost cylinder (outer tube) depends on the number of layer configurations, but is typically in a range of 1 mm to 100 mm and preferably in a range of 3 mm to 30 mm. The equivalent diameter of a middle tube between the minimum cylinder and the outermost cylinder can be appropriately adjusted based on the equivalent diameters of the inner tube and the outer tube.

The multilayer cylindrical mixer which can be used can be produced by combining a joint such as BORED-THROUGH UNION TEE (manufactured by Swagelok Company) with a tube having an optional inner diameter and an optional outer shape. Further, a known structure such as a structure described in JP2006-096569A can be used as a multilayer cylindrical mixer.

[Reaction Flow Path]

The solutions merged in the merging region (3) circulate through the reaction flow path (4). At the time of circulation in the reaction flow path after the solutions are merged, the copper salt reacts with the basic compound to generate copper hydroxide, and cupric oxide is deposited in the form of fine particles due to the dehydration reaction by being heated.

It is preferable that the reaction flow path (4) is tubular. As the reaction flow path (4), a tube having an equivalent diameter of 0.1 cm to 50 cm (preferably in a range of 0.1 cm to 10 cm) and a length of 20 cm to 50 m is typically used. The cross-sectional shape of the reaction flow path (4) is not particularly limited, and examples thereof include a circular shape and may have any of an elliptical shape, a rectangular shape, or a square shape. From the viewpoint that the liquid pool is unlikely to occur in the tube, it is more preferable that the cross-sectional shape of the tube in the T-shaped mixer is circular.

The material of the tube constituting the reaction flow path (4) is not particularly limited, and examples thereof include perfluoroalkoxyalkane (PFA), TEFLON (registered trademark), an aromatic polyether ketone-based resin, stainless steel, copper (or an alloy thereof), nickel (or an alloy thereof), titanium (or an alloy thereof), quartz glass, and lime soda glass. From the viewpoints of the flexibility and the chemical resistance, PFA, TEFLON (registered trademark), stainless steel, nickel alloy (hastelloy), or titanium is preferable as the material of the tube.

[Reaction for Generating Copper Oxide Fine Particles]

The copper salt in the copper salt solution and the basic compound in the basic compound solution, which are merged with each other in the merging region (3), react with each other to generate copper hydroxide while circulating through the reaction flow path (4) and are dehydrated by being heated to generate cupric oxide. The cupric oxide is deposited in the form of fine particles in the solution in the reaction flow path. The copper oxide fine particles generated in the reaction flow path are recovered in the recovery container 7 as a copper oxide fine particle dispersion liquid.

The copper salt to be used is not particularly limited as long as the copper salt is dissolved in a solvent of a copper salt solution. For example, a copper salt selected from copper (II) nitrate, copper (II) chloride, copper (II) bromide, copper (II) iodide, copper (II) sulfate, copper (II) formate, copper (II) acetate, copper (II) propionate, copper (II) isobutyrate, copper (II) oleate, copper (II) citrate, copper (II) phthalate, copper (II) oxalate, copper (II) tartrate, basic copper carbonate, and basic copper sulfate, and hydrates of these, an inorganic compound complex of copper (such as a tetraamine copper complex), and an organic compound complex of copper (such as copper acetylacetonate) can be used. These may be used alone or in the form of a mixture of two or more kinds thereof. Among these, a copper salt selected from copper (II) formate, copper (II) acetate, a copper (II) acetate hydrate, copper (II) propionate, copper (II) isobutyrate, copper (II) oleate, copper (II) citrate, copper (II) phthalate, copper (II) oxalate, copper (II) tartrate, and hydrates of these is preferable, and copper (II) acetate or a copper (II) acetate hydrate is more preferable.

As described below, it is speculated that copper oxide fine particles having excellent dispersibility are obtained by protecting the charge of copper oxide fine particles using the organic layer (c) derived from acetic acid or an acetate so that aggregation of particles is prevented. Therefore, from the viewpoint of protecting the charge, it is preferable to use copper (II) acetate or a copper (II) acetate hydrate as the copper salt.

The basic compound to be used is not particularly limited as long as salt exchange with a copper salt is carried out and copper hydroxide can be generated. For example, a basic compound selected from lithium hydroxide (LiOH), sodium hydroxide (NaOH), potassium hydroxide (KOH), ammonia, methylamine, dimethylamine, trimethylamine, tetramethylamine hydroxide, ethylamine, diethylamine, trimethylamine, and tetraethylamine hydroxide can be used. These may be used alone or in the form of a mixture of two or more kinds thereof. Among these, sodium hydroxide is preferable.

The solvent used for the copper salt solution and the basic compound solution is not particularly limited as long as the copper salt and the basic compound can be dissolved therein, and examples thereof include water, an organic solvent, and a mixture of water and an organic solvent.

As the organic solvent, a water-soluble organic solvent is preferable, and specific examples thereof include an alcohol such as methanol or ethanol, a ketone such as acetone, methyl ethyl ketone, and tetrahydrofuran.

Further, ethylene glycol having two or more hydroxyl groups in a molecule, diethylene glycol, 1,2-propanediol, 1,3-propanediol, 1,2-butanediol, 1,3-butanediol, 1,4-butanediol, 2,3-butanediol, pentanediol, hexanediol, octanediol, polyethylene glycol, or glycerol can also be used.

The organic solvent may be used alone or in the form of a mixture of two or more kinds thereof.

As the solvent used for the copper salt solution and the basic compound solution, water or an alcohol solution is preferable, and water is more preferable. In other words, it is preferable that the copper salt solution and the basic compound solution are respectively a copper salt aqueous solution and a basic compound aqueous solution. Further, ultrapure water having a specific resistance value of 18

MΩ·cm or greater is preferable as water used for the copper salt aqueous solution and the basic compound aqueous solution.

In a case where the copper salt reacts with the basic compound, copper hydroxide is generated. As an example, this reaction is represented by Formula (i) by employing copper (II) nitrate as a copper salt and sodium hydroxide as a basic compound.

$$Cu(NO_3)_2 + 2NaOH \rightarrow Cu(OH)_2 + 2NaNO_3 \qquad \text{Formula (i)}$$

The copper hydroxide generated in the above-described manner is continuously dehydrated by being heated, and cupric oxide is deposited in the form of fine particles. This reaction is represented by Formula (ii).

$$Cu(OH)_2 \rightarrow CuO + H_2O \qquad \text{Formula (ii)}$$

The dehydration reaction represented by Formula (ii) efficiently proceeds at a high temperature. Therefore, according to the method of producing the fine particles according to the embodiment of the present invention, it is preferable that the reaction (that is, the reaction from the contact between the copper salt and the basic compound to generation of cupric oxide) between the copper salt and the basic compound is carried out at 70° C. or higher (more preferably 80° C. or higher, still more preferably 90° C. or higher, and even still more preferably in a range of 90° C. to 100° C.). In other words, it is preferable that a heating region (8) is provided from the merging portion (3) to the reaction flow path as illustrated in FIGS. 1, 3, and 6. The heating region (8) can be provided using a water bath, an oil bath, a thermostat, or the like. By setting the reaction temperature to 80° C. or higher, formation of secondary aggregates from the obtained copper oxide fine particles can be suppressed.

It is considered that, in a case where the reaction of generating $Cu(OH)_2$ is applied to a flow type reaction system, the flow path tends to be blocked because $Cu(OH)_2$ which is generated by Formula (i) tends to gel. However, the present inventors found that generated $Cu(OH)_2$ can be rapidly dehydrated and converted into cupric oxide by practically applying the reaction to the flow type reaction system, and thus the reaction system of stably and continuously producing cupric oxide can be constructed.

Further, in order to suppress aging (particle growth) of the copper oxide fine particle dispersion to be obtained, it is preferable that the reaction flow path positioned on the downstream side of the heating region (8) is disposed in a cooling region (9). It is preferable that the temperature of the cooling region is set to be in a range of 0° to 30° C. The cooling region (9) can be made into, for example, a region of cooling the reaction flow path.

According to the method of producing the fine particles according to the embodiment of the present invention, in the merging portion (merging portion J) where the copper salt solution circulating through the first flow path and the basic compound solution circulating through the second flow path are merged with each other, the relationship of Expression (1) is satisfied in a case where the concentration of the copper (II) salt solution circulating through the first flow path is set as W in the unit of mol/L, the flow rate of the copper (II) salt solution circulating through the first flow path is set as X in the unit of mL/min, the concentration of the basic compound solution circulating through the second flow path is set as Y in the unit of mol/L, the flow rate of the basic compound solution circulating through the second flow path is set as Z in the unit of mL/min, and the valence of the basic compound circulating through the second flow path is set as V.

$$1.5 \geq [Y \times Z \times V]/[W \times X] \geq 1.1 \qquad \text{Expression (1)}$$

Here, in a case where a state in which the copper salt solution having circulated through the first flow path per unit time is homogeneously mixed with the basic compound solution having circulated through the second flow path per unit time is assumed, the relationship of Expression (1) in the merging portion J indicates the ratio of the molar equivalent of the basic compound to the molar equivalent of the copper salt in the solution in the state in which the solutions are homogeneously mixed. Further, in a case where the copper salt solution and the basic compound solution are introduced into two or more of (a plurality of) flow paths and circulate therethrough, sum values in each flow path through which the copper salt solution circulates and sum values in each flow path through which the basic compound solution circulates are respectively used as W, X, Y, and Z.

The "valence of the basic compound" indicates the number of protons which can be accepted by one molecule of the basic compound that is a solute of the basic compound solution or the number of hydroxide ions which can be released by one molecule. For example, sodium hydroxide or ammonia is monovalent (valence of 1) and calcium hydroxide or ethylenediamine is divalent (valence of 2).

By adjusting $[Y \times Z \times V]/[W \times X]$ in the merging portion J to be in a specific range, the shape of copper oxide fine particles to be obtained can be controlled to be a desired shape. For example, spherical copper oxide fine particles are obtained in a case where $[Y \times Z \times V]/[W \times X]$ in the merging portion J is decreased, rod-like copper oxide fine particles are obtained in a case where $[Y \times Z \times V]/[W \times X]$ is increased, and plate-like copper oxide fine particles are obtained in a case where $[Y \times Z \times V]/[W \times X]$ is further increased. In a case where W, X, Y, Z, and V in the merging portion J satisfy the relationship of Expression (1), fine particles in which the average particle diameter of copper oxide fine particles to be obtained is set to 70 nm or less can be obtained.

Further, it is preferable that Expression (1) in the merging portion J is Expression (2) shown below.

$$1.5 > [Y \times Z \times V]/[W \times X] \geq 1.3 \qquad (2)$$

W: concentration (mol/L) of copper (II) salt solution circulating through first flow path X: flow rate (mL/min) of copper (II) salt solution circulating through first flow path Y: concentration (mol/L) of basic compound solution circulating through second flow path Z: flow rate (mL/min) of basic compound solution circulating through second flow path V: valence of basic compound circulating through second flow path The detailed reason is not clear, but it is considered that copper oxide fine particles, each of which has a surface on which a monovalent copper compound has been formed, are obtained in a case where W, X, Y, Z, and V in the merging portion J satisfies Expression (1) and preferably Expression (2).

The flow rate of the liquid circulating through the flow path on the upstream side of the merging portion and the flow rate of the solution circulating through the reaction flow path are not particularly limited and are appropriately adjusted depending on the equivalent diameter, the length, and the like of the flow path. For example, the flow rate of the liquid circulating through each flow path can be set to be in a range of 1 mL/min to 1000 mL/min and preferably in a range of 2 mL/min to 400 mL/min. Further, the flow rate is also set to be more preferably in a range of 3 mL/min to 200 mL/min, still more preferably in a range of 4 mL/min to 100 mL/min, even still more preferably in a range of 4 mL/min to 50 mL/min, and particularly preferably in a range of 5 mL/min to 30 mL/min. In addition, the flow rates of the liquid circulating through each flow path on the upstream side of the merging portion may be same as one another in each flow path or different from one another for each flow path.

The linear velocity of the liquid circulating through the flow path on the upstream side of the merging portion and the linear velocity of the solution circulating through the reaction flow path are set to be preferably in a range of 2 to 10000 mm/sec and more preferably in a range of 20 to 500 mm/sec.

In a case where a multilayer cylindrical mixer is disposed in the merging region (3), it is preferable that the ratio of a linear velocity a1 of the solution circulating through the minimum cylinder (inner tube) of the multilayer cylindrical mixer to a linear velocity b1 of the solution (that is, the solution circulating through the space between a cylinder other than the minimum cylinder and an inner cylinder adjacent to a cylinder other than this minimum cylinder) circulating through a cylinder other than the minimum cylinder satisfies "a1/b1=1 to 10000", more preferable that the ratio thereof satisfies "a1/b1=0.01 to 100", and still more preferable that the ratio thereof satisfies "a1/b1=0.02 to 50". In a case where the linear velocity of the solution circulating through each cylinder is set to be in the above-described preferable range, the pressure loss at the time of sending a liquid can be reduced, and each liquid can be allowed to stably circulate.

In a case where a two-layer cylindrical mixer is disposed in the merging region (3), it is preferable that the ratio of a linear velocity a2 of the solution circulating through the minimum cylinder (inner tube) of the two-layer cylindrical mixer to a linear velocity b2 of the solution (that is, the solution circulating through the space between the outer tube and the inner tube) circulating through a cylinder (outer tube) other than the minimum cylinder satisfies "a2/b2=0.02 to 50", more preferable that the ratio thereof satisfies "a2/b2=0.05 to 20", and still more preferable that the ratio thereof satisfies "a2/b2=0.1 to 10". In a case where the linear velocity of the solution circulating through each cylinder is set to be in the above-described preferable range, the pressure loss at the time of sending a liquid can be reduced, and each liquid can be allowed to stably circulate.

The concentration of the copper salt solution circulating through the first flow path is not particularly limited, but there is a concern that the content of the copper (II) oxide to be generated is decreased and the load of a process of concentrating and recovering particles is increased in a case where the concentration thereof is small. On the contrary, in a case where the concentration thereof is high, the viscosity of a liquid is increased and the mixing properties of the mixer are degraded in some cases. Therefore, the concentration of the copper salt solution is preferably in a range of 0.01 to 5 mol/L and more preferably in a range of 0.02 to 1 mol/L.

From the above-described viewpoints, the concentration of the basic compound solution circulating through the second flow path is preferably in a range of 0.02 to 10 mol/L and more preferably in a range of 0.04 to 4 mol/L.

By allowing W, X, Y, Z, and V in the merging portion J to satisfy the relationship of Expression (1), copper oxide fine particles having a small average particle diameter are obtained without using a reducing agent, but a reducing agent of reducing copper (II) ions can be used as necessary.

The amount of the reducing agent to be used is not particularly limited, and is preferably in a range of 0 to 1 mol and more preferably in a range of 0.01 to 0.5 mol based on 1 mol of copper oxide, from the viewpoint of obtaining copper oxide fine particles having a smaller average particle diameter.

The reducing agent can be added to the basic compound solution.

The kind of the reducing agent is not particularly limited, and a known reducing agent can be used. Examples thereof include hydroxylamine sulfate, hydroxylamide nitrate, sodium sulfite, sodium bisulfate, sodium dithionite, hydrazine sulfate, hydrazine phosphate, hydrazine, hypophosphorous acid, and sodium hypophosphite. These may be used alone or in combination of two or more kinds thereof. Among these, hydrazine is preferable as the reducing agent.

By allowing W, X, Y, Z, and V in the merging portion J to satisfy the relationship of Expression (1), copper oxide fine particles having high dispersibility are obtained without using a dispersant, but a known additive such as a dispersant or a dispersion stabilizer can be used as necessary.

The dispersant can be added to the copper salt solution.

As the dispersant which can be used, for example, an anionic, cationic, amphoteric, or non-ionic dispersant, or a low-molecular-weight or high-molecular-weight dispersant can be used. Preferred examples thereof include sodium hexametaphosphate. The amount of the dispersant to be added may be appropriately adjusted depending on the type of the dispersant, but the amount of the dispersant to be added to the dispersion liquid is preferably in a range of 0% to 10% by mass (wt %) and more preferably in a range of 0% to 8% by mass.

The copper oxide fine particles of the present invention and the dispersion liquid in which the copper oxide fine particles have been dispersed may be used for antibacterial and antiviral applications other than the deodorant application.

Hereinafter, the present invention will be described in more detail based on the following examples, but the present invention is not limited to these examples.

EXAMPLES

Production of Fine Particles 1 and Dispersion Liquid 1 Thereof

<Construction of Flow Type Reaction System>

A flow type reaction system having a configuration illustrated in FIG. 1 was constructed. As the first flow path (1), the second flow path (2), and the reaction flow path (4), tubes made of SUS316 were used. Syringe pumps (PHD ULTRA, manufactured by HARVARD Apparatus) were used as the copper salt solution introduction means (5) and the basic compound solution introduction means (6), and a configuration in which a syringe (volume of 100 mL) filled with the copper salt aqueous solution and a syringe (volume of 100 mL) filled with the basic compound aqueous solution were respectively mounted on each syringe pump was employed.

The tip of the syringe filled with the copper salt solution was connected to the first flow path having an outer diameter of ⅛ In (3.18 mm) and an inner diameter of 2.17 mm. Further, the tip of the syringe filled with the basic compound solution was connected to the second flow path having an outer diameter of ⅛ In (3.18 mm) and an inner diameter of 2.17 mm. A pressure gauge was installed in the second flow path so that the pressure inside the flow path at the time of sending a liquid was able to be measured.

In the region on the downstream side in the first flow path (1), a tube having a length of 50 cm, an outer diameter of 1/16 In (1.59 mm), and an inner diameter of 1 mm was wound in a coil shape and disposed in the heating region (8, oil bath). Further, similar to the region on the downstream side in the second flow path (2), a tube having a length of 50 cm, an outer diameter of 1/16 In (1.59 mm), and an inner diameter of 1 mm was wound in a coil shape and disposed in the heating region (8).

A T-shaped mixer (manufactured by Upchurch Scientific Inc.) having an inner diameter of 0.5 mm was installed at the ends of the first flow path (1) and the second flow path (2) on the downstream side, and the opening portions (A and B) of the T-shaped mixer (trade name: TEE UNION, manufactured by Upchurch Scientific Inc.) were connected to each flow path such that the copper salt solution and the basic compound solution collided with each other. The remaining opening portion O of the T-shaped mixer was connected to a flow path wound in a coil shape and having a length of 2 m, an outer diameter of ⅛ In (3.18 mm), and an inner diameter of 2.17 mm, and this flow path was installed in the heating region (8, water bath (20° C.)). Further, a flow path wound in a coil shape and having a length of 1 m, an outer diameter of ⅛ In (3.18 mm), and an inner diameter of 2.17 mm was connected to the downstream side of the heating region, and this flow path was installed in the cooling region (9). The recovery container (7) was installed on the downstream side of the cooling region (9), and the reaction solution was recovered.

Fine Particles 1 and Dispersion Liquid 1 Thereof

A copper (II) acetate hydrate was dissolved in water and diluted with water to prepare a copper acetate aqueous solution (concentration of 0.285 mol/L). A 50% (mass/volume) sodium hydroxide aqueous solution was diluted with water to prepare a sodium hydroxide aqueous solution (concentration of 0.399 mol/L).

Each glass syringe (volume of 100 mL) was filled with 100 mL of the copper acetate aqueous solution as the copper (II) salt solution and 100 mL of the sodium hydroxide aqueous solution as the basic compound solution and was provided in the syringe pump of the flow type reaction system. Each liquid was sent at 5 ml/min. In this flow type reaction system, the temperature of the heating region (8) was set to 90° C. 100 mL of the liquid (dispersion liquid 1) having passed through the reaction flow path was recovered in the recovery container (a polyethylene container having a volume of 250 ml). The content of the copper oxide fine particles in the dispersion liquid 1 was 0.11% by mass.

130 mL of the obtained dispersion liquid was centrifuged at approximately 10000 the fine particles were precipitated, and the obtained paste was dried in a vacuum at 40° C. for 5 hours, thereby obtaining dry powder of fine particles 1 having an average primary particle diameter of 7 nm.

Fine Particles 2 to 4 and Dispersion Liquids 2 to 4 Thereof

Fine particles 2 to 4 and dispersion liquids 2 to 4 were obtained in the same manner as that for the fine particles 1 and the dispersion liquid 1 except that the concentration (mol/L) W of the copper (II) salt solution circulating through the first flow path and the concentration (mol/L) Y of the basic compound solution circulating through the second flow path were changed into those listed in Table 1.

In the dispersion liquids 2 to 4, the contents of the copper oxide fine particles were respectively 0.12% by mass, 0.13% by mass, and 0.15% by mass.

TABLE 1

| No. | Raw material | Cu molar concentration M (W) | NaOH molar concentration M (Y) | Valence of NaOH (V) | Molar ratio between NaOH and copper raw materials | Flow rate of Cu (X) and NaOH (Z) ml/min | Ratio between flow rates | $[Y \times Z \times V]/[W \times X]$ | |
|---|---|---|---|---|---|---|---|---|---|
| 1 | Copper acetate | 0.285 | 0.399 | 1 | 1.4 | 45 | 1 | 1.4 | Example |
| 2 | Copper acetate | 0.285 | 0.427 | 1 | 1.5 | 45 | 1 | 1.5 | Example |
| 3 | Copper acetate | 0.285 | 0.484 | 1 | 1.7 | 45 | 1 | 1.7 | Example |
| 4 | Copper acetate | 0.285 | 2.280 | 1 | 8.0 | 45 | 1 | 8.0 | Comparative Example |

W: concentration (mol/L) of copper (II) salt solution circulating through first flow path
X: flow rate (mL/min) of copper (II) salt solution circulating through first flow path
Y: concentration (mol/L) of basic compound solution circulating through second flow path
Z: flow rate (mL/min) of basic compound solution circulating through second flow path
V: valence of basic compound circulating through second flow bath Fine Particles 6 and Dispersion Liquid 6 Thereof
(Comparative Example)

Copper oxide fine particles (copper (II) oxide, Kanto Chemical Co., Inc., COPPER OXIDE (Cat No. 07504 to 07543, Mw: 79.55)) were dried at a low temperature for 40 hours under reduced pressure by setting the temperature to 4° C., and the moisture was removed therefrom, thereby obtaining fine particles 6.

The fine particles 6 were dissolved in pure water, and the solution was uniformly stirred for 30 minutes using a magnetic stirrer, thereby obtaining a 0.11 mass % dispersion liquid 6.

Fine Particles 5 and Dispersion Liquid 5
(Comparative Example)

10% by mass of sodium hexametaphosphate was added to copper oxide fine particles dispersed in the dispersion liquid 6, and a shearing treatment was performed on the dispersion liquid 6 under conditions of 21500 rpm for 120 minutes using a disperser (CLEARMIX 2.2S, manufactured by MTECHNIQUE Co., Ltd.), thereby obtaining a dispersion liquid 5.

The dispersion liquid 5 was dried at a low temperature for 40 hours under reduced pressure by setting the temperature to 40° C., and the moisture was removed therefrom, thereby obtaining dry powder.

<Observation and Physical Properties of Fine Particles>
(Peak Area Ratio (1))

The dry powder of the fine particles 1 obtained in the above-described manner was measured under the following conditions according to X-ray photoelectron spectroscopy (XPS).

Figure 9:
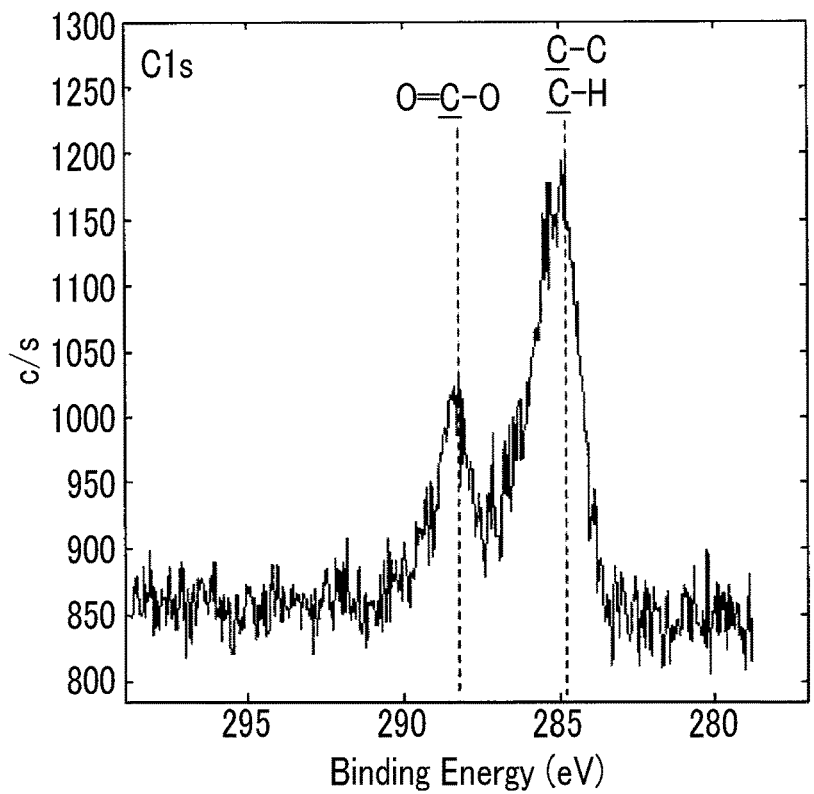
FIG. 9 shows XPS measurement data for fine particles 1 of examples and is related to carbon C1s.
Figure 10:
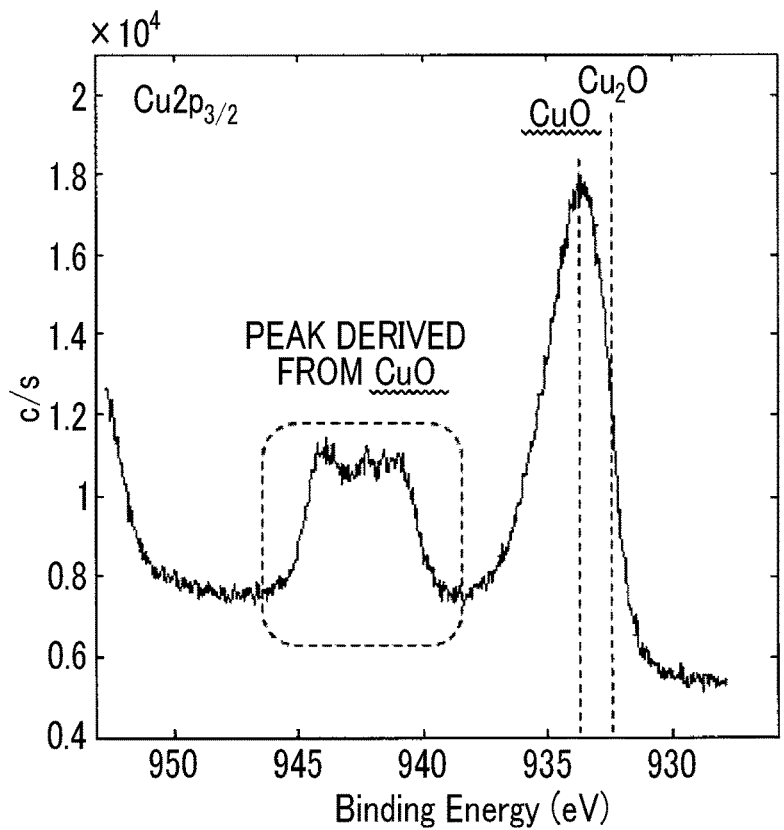
FIG. 10 shows XPS measurement data for fine particles 1 of examples and is related to copper $Cu2p_{3/2}$.
Figure 11:
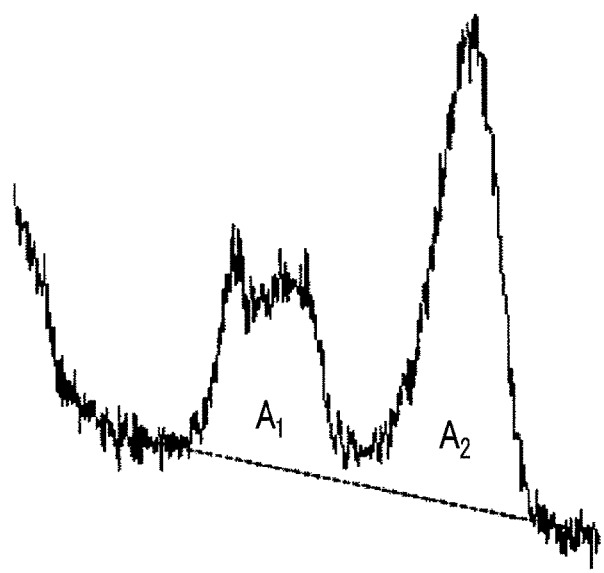
FIG. 11 shows an area $A_1$ of a peak derived from divalent CuO in the XPS measurement data and an area $A_2$ of a peak derived from all components containing Cu.

The C1s peak derived from a trace amount of contamination present on the surface was calibrated to 284.8 eV (FIG. 9), and the peak area ratio was calculated by setting the area of a peak derived from divalent CuO in a range of 938.5 eV to 948 eV as $A_1$ and the area of a peak derived from all components containing Cu in a range of 928 eV to 938.5 eV as $A_2$ based on 938.5 eV in the spectrum of $Cu2p_{3/2}$ shown in FIG. 10. The range of the peak area $A_1$ and the range of the peak area $A_2$ were set as shown in FIG. 11.

The abundance ratio of cuprous oxide in the fine particles was acquired from the following calculation formula as the peak area ratio (1).

Peak area ratio $(1) = A_1/(A_1+A_2)$

As the result, it was confirmed that the copper oxide fine particles were fine particles respectively having a surface on which cuprous oxide had been formed based on the fact that the calculated value of the peak area ratio (1) was 0.04.

XPS Measurement Conditions:
X-ray source: monochromatic Al-Kα rays (100 μmφ), 25 W, 15 kV)
Charge correction: possible (combination of electron gun and slow ion gun)
Photoelectron extraction angle: 45°
Measurement range: 300 μm2 (area)
Pass Energy: 23.5 eV
Measurement elements: Cu2p, Cu LMM, C1s
Energy correction: correction of C1s to 284.8 eV (Measurement of DLS Average Particle Diameter (Average Secondary Particle Diameter))

The DLS (dynamic light scattering) average particle diameter in the dispersion liquid 1 obtained by performing the above-described treatment was measured using a dynamic light scattering determination device (ZETASIZER ZS, manufactured by Malvern Instruments Ltd.). The average particle diameter was measured according to a method defined in ISO13321 as the average value (Z-Average) of the particle diameter based on cumulant analysis.

The dispersion liquid 1 was diluted with water so that the concentration thereof was set to 0.01% by mass, and the average secondary particle diameter (nm) thereof was measured.

(Measurement of Zeta Potential)
An ultrafiltration membrane (molecular weight cutoff of 10000, manufactured by Toyo Roshi Kaisha, Ltd.) was provided for a stirring type ultra-holder (model number: UHP-76K, manufactured by Toyo Roshi Kaisha, Ltd.), ultrafiltration was performed on the dispersion liquid 1 while water having a pH of 6.8 was added thereto, thereby preparing a 0.01 mass % dispersion liquid. By performing filtration, impurities such as ions were removed and a predetermined conductivity was obtained. A predetermined amount of the dispersion liquid was introduced into a dedicated measurement cell made of glass, and the zeta potential (mV) was measured using ELSZ1EAS (manufactured by OTSUKA ELECTRONICS Co., Ltd.).

(Measurement of Specific Surface Area)
The specific surface area (m2/g) of the fine particles 1 obtained in the above-described manner was acquired under the following conditions.
Pre-treatment: dried under reduced pressure at 40° C. for 40 hours
Measurement device: Quantachrome ChemBET3000
Measuring method: BET one-point method, 30% of nitrogen and helium were used (Deodorant Test)
The $H_2S$ removal rate (%) of the fine particles 1 obtained in the above-described manner was acquired.

The $H_2S$ removal rate was acquired by measuring the concentration of $H_2S$ in a Tedlar bag filled with odor gas under the following conditions using the fine particles 1 applied to filter paper and performing calculation based on the following equation.

$H_2S$ removal rate=(concentration ppm of remaining $H_2S$)/(concentration ppm of initial $H_2S$)×100

Coating amount of fine particles 1: 0.06 mg in 100 cm2
Test method, standard: fiber cooperative act, detection tube method
Odor gas type: 20 ppm of hydrogen sulfide
Dilution gas condition: mixed with dry $N_2$ gas, and humidity control carried out under temperature condition of 20° C. at humidity of 65% for 24 hours or longer (as defined in fiber cooperative act)
Time for exposure to odor gas: 2 hours
Volume of Tedlar bag filled with the odor gas: 3 L
As the filter paper used in the test, commercially available cellulose filter paper having a basis weight of 450 g/m² and a thickness of 1.5 mm was used.

Figure 12:
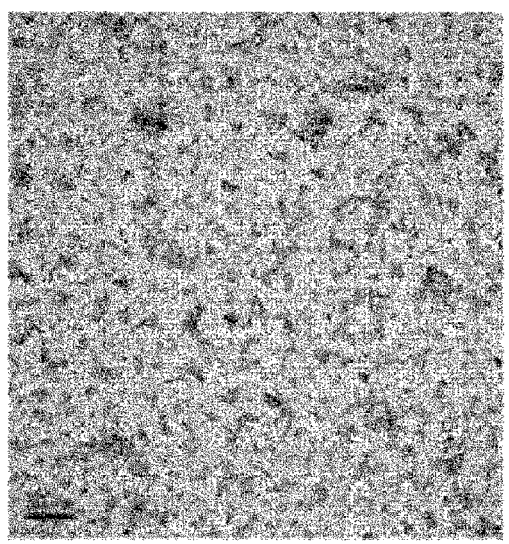
FIG. 12 shows photomicrographs of fine particles 1 of examples and fine particles 4 of comparative examples.
Figure 12:
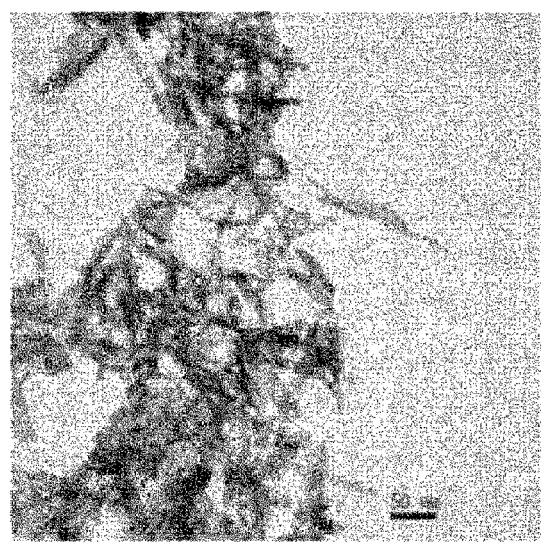

The fine particles 2 to 6 and the dispersion liquids 2 to 6 thereof were observed and the physical properties were measured in the same manner as that for the fine particles 1 and the dispersion liquid 1 thereof, and the results are listed in Table 2. Further, the photomicrographs of the fine particles 1 and the fine particles 4 are shown in FIG. 12.

TABLE 2

| No. | Average primary particle diameter (nm) | Average secondary particle diameter (nm) | Specific surface area (m²/g) | Zeta potential mV | Peak area ratio (1) | H₂S removal rate % | |
|---|---|---|---|---|---|---|---|
| 1 | 7 | 40 | 160 | +39 | 0.04 | 87 | Example |
| 2 | 10 | 45 | 128 | +45 | 0.05 | 78 | Example |
| 3 | 20 | 50 | 105 | +31 | 0.07 | 60 | Example |
| 4 | 80 | 250 | 86 | Impossible to measure (#1) | 0.25 | 40 | Comparative Example |
| 5 | 100 | 130 | 17 | −50 | 0.25 | 17 | Comparative Example |
| 6 | 130 | 300 | 14 | Impossible to measure (#1) | 0.14 | 8 | Comparative Example |

As described above, it was found that the fine particles according to the embodiment of the present invention show a high H₂S removal rate and have an excellent deodorizing effect.

According to the present invention, it is possible to provide nanometer-sized fine particles having an excellent deodorizing effect. Further, the dispersion liquid containing the fine particles according to the embodiment of the present invention and the deodorizer containing the fine particles and the dispersion liquid are capable of preventing aggregation of the fine particles and exhibiting an excellent deodorizing effect.

The present invention has been described in detail with reference to the specific embodiments, and it is apparent to those skilled in the art that various changes and modifications can be made without departing from the spirit and the scope of the present invention.

EXPLANATION OF REFERENCES

100, 200, 300: flow type reaction system
1: first flow path
2: second flow path
3: merging region
3a: T-shaped mixer
3b: two-layer cylindrical mixer (multilayer cylindrical mixer)
3c: three-layer cylindrical mixer (multilayer cylindrical mixer)
4: reaction flow path
5: copper salt solution introduction means (syringe pump)
6: basic compound solution introduction means (syringe pump)
7: recovery container
8: heating region
9: cooling region
P: pressure gauge
J: merging portion
T1: inner tube
T2: outer tube
T3: middle tube
10: third flow path
11: third liquid introduction means (syringe pump)

What is claimed is:

1. A fine particle in which a surface of a copper oxide fine particle (a) is coated with a coating layer (b) containing a monovalent copper compound,
    wherein the fine particle has a specific surface area of 100 m²/g or greater,
    an average primary particle diameter in a range of 5 to 10 nm, and
    an average secondary particle diameter in a range of 5 to 50 nm.

2. The fine particle according to claim 1,
    wherein a surface of the coating layer (b) containing a monovalent copper compound is further coated with an organic layer (c) derived from an acetic acid or an acetate.

3. The fine particle according to claim 1,
    wherein the monovalent copper compound is a cuprous oxide.

4. The fine particle according to claim 2,
    wherein the monovalent copper compound is a cuprous oxide.

5. The fine particle according to claim 1,
    wherein the following peak area ratio (1) of the fine particle in X-ray diffraction using a CuKα as an X-ray source is in a range of 0.01 to 0.10, Peak area ratio (1)=$A_1/(A_1+A_2)$ wherein $A_1$ is a peak area of a peak derived from a divalent CuO in a range of 938.5 eV to 948 eV; and
    $A_2$ is a peak area of a peak derived from all components containing Cu in a range of 928 eV to 938.5 eV.

6. The fine particle according to claim 2,
    wherein the following peak area ratio (1) of the fine particle in X-ray diffraction using CuKα as an X-ray source is in a range of 0.01 to 0.10, Peak area ratio (1)=$A_1/(A_1+A_2)$ wherein $A_1$ is a peak area of a peak derived from a divalent CuO in a range of 938.5 eV to 948 eV; and
    $A_2$ is a peak area of a peak derived from all components containing Cu in a range of 928 eV to 938.5 eV.

7. The fine particle according to claim 3,
    wherein the following peak area ratio (1) of the fine particle in X-ray diffraction using CuKα as an X-ray source is in a range of 0.01 to 0.10, Peak area ratio (1)=$A_1/(A_1+A_2)$ wherein $A_1$ is a peak area of a peak derived from a divalent CuO in a range of 938.5 eV to 948 eV; and
    $A_2$ is a peak area of a peak derived from all components containing Cu in a range of 928 eV to 938.5 eV.

8. The fine particle according to claim 4, wherein the following peak area ratio (1) of the fine particle in X-ray diffraction using CuKα as an X-ray source is in a range of 0.01 to 0.10, $$\text{Peak area ratio (1)} = A_1/(A_1+A_2)$$

wherein $A_1$ is a peak area of a peak derived from a divalent CuO in a range of 938.5 eV to 948 eV; and $A_2$ is a peak area of a peak derived from all components containing Cu in a range of 928 eV to 938.5 eV.

9. The fine particle according to claim 1,
wherein the fine particle has a zeta potential of 30 mV to 50 mV in a case of being dispersed in water having a pH of 6.8.

10. The fine particle according to claim 2,
wherein the fine particle has a zeta potential of 30 mV to 50 mV in a case of being dispersed in water having a pH of 6.8.

11. The fine particle according to claim 3,
wherein the fine particle has a zeta potential of 30 mV to 50 mV in a case of being dispersed in water having a pH of 6.8.

12. The fine particle according to claim 4,
wherein the fine particle has a zeta potential of 30 mV to 50 mV in a case of being dispersed in water having a pH of 6.8.

13. A dispersion liquid which is formed by dispersing the fine particle according to claim 1 in a dispersion medium,
wherein a content of the fine particle in the dispersion liquid is in a range of 0.0001% to 14% by mass.

14. A dispersion liquid which is formed by dispersing the fine particle according to claim 2 in a dispersion medium,
wherein a content of the fine particle in the dispersion liquid is in a range of 0.0001% to 14% by mass.

15. The dispersion liquid according to claim 13,
wherein an average particle diameter of the fine particle in the dispersion liquid according to a dynamic light scattering method is in a range of 5 to 50 nm.

16. The dispersion liquid according to claim 14,
wherein an average particle diameter of the fine particle in the dispersion liquid according to a dynamic light scattering method is in a range of 5 to 50 nm.

17. A deodorizer comprising:
the fine particle according to claim 1.

18. A deodorizer comprising:
the fine particle according to claim 2.

19. A deodorizer comprising:
the dispersion liquid according to claim 13.

20. A deodorizer comprising:
the dispersion liquid according to claim 14.

* * * * *